(12) United States Patent
Chiu et al.

(10) Patent No.: US 11,328,419 B2
(45) Date of Patent: May 10, 2022

(54) PORTABLE BIOLOGICAL MICROSCOPIC IMAGE ANALYSIS SYSTEM

(71) Applicant: National Applied Research Laboratories, Hsinchu (TW)

(72) Inventors: Chih-Hsien Chiu, Hsinchu (TW); Chia-Yung Jui, Hsinchu (TW); Shu-Hui Hung, Hsinchu (TW); Peggy Joy Lu, Hsinchu (TW)

(73) Assignee: National Applied Research Laboratories, Hsinchu (TW)

( * ) Notice: Subject to any disclaimer, the term of this patent is extended or adjusted under 35 U.S.C. 154(b) by 115 days.

(21) Appl. No.: 17/035,019

(22) Filed: Sep. 28, 2020

(65) Prior Publication Data

US 2021/0183057 A1    Jun. 17, 2021

(30) Foreign Application Priority Data

Dec. 13, 2019    (TW) ................................ 108216562

(51) Int. Cl.

| | |
|---|---|
| *G06T 7/00* | (2017.01) |
| *G02B 21/36* | (2006.01) |
| *G16H 30/40* | (2018.01) |
| *G06F 16/51* | (2019.01) |
| *G16H 10/40* | (2018.01) |
| *G06V 20/69* | (2022.01) |

(52) U.S. Cl.
CPC .......... *G06T 7/0012* (2013.01); *G02B 21/365* (2013.01); *G06F 16/51* (2019.01); *G06V 20/693* (2022.01); *G06V 20/695* (2022.01); *G16H 10/40* (2018.01); *G16H 30/40* (2018.01); *G06T 2207/10056* (2013.01); *G06T 2207/20081* (2013.01); *G06T 2207/30024* (2013.01)

(58) Field of Classification Search
CPC ......... G06T 7/0012; G06T 2207/10056; G06T 2207/20081; G06T 2207/30024; G02B 21/365; G02B 21/0008; G02B 21/086; G02B 21/14; G06F 16/51; G06F 16/54; G06V 20/693; G06V 20/695; G06V 10/17; G06V 20/698; G16H 10/40; G16H 30/40

See application file for complete search history.

(56) References Cited

U.S. PATENT DOCUMENTS

2020/0049945 A1*    2/2020  Brace ........................ G06F 9/30

* cited by examiner

*Primary Examiner* — Nam D Pham
(74) *Attorney, Agent, or Firm* — James W. Huffman; Huffman Law Group, PC

(57) ABSTRACT

A portable biological microscopic image analysis system is suitable for analyzing a sample on a slide in real time, and the sample comes from an animal. The portable biological microscopic image analysis system includes a handheld electronic device and a microscope kit; the handheld electronic device includes an image capture unit, an image analysis module electrically connected to the image capture unit, and a real-time state analysis module electrically connected to the image analysis module; the microscope kit is detachably mounted on the handheld electronic device; wherein the image capture unit is used to obtain an image related to the sample through the microscope kit, the image analysis module is used to obtain cell information corresponding to the animal according to the image, and the real-time state analysis module is used to obtain state information corresponding to the animal according to the cell information.

10 Claims, 4 Drawing Sheets

PORTABLE BIOLOGICAL MICROSCOPIC IMAGE ANALYSIS SYSTEM

TECHNICAL FIELD

The present invention relates to an analysis system, in particular to a portable biological microscopic image analysis system.

BACKGROUND ART

Prior animal breeders, such as dairy farmers, often required professional consultations to assist in identifying the quality of the animal's sperm cells, pairing the animals, and providing the animals with other treatments; the method for the identification of the cells was to sample the animals in the field, bring the sample back to a laboratory, and observe it with a huge fluorescence microscope.

Due to the bulky size of the fluorescent microscope and the limitation to fixed-spot observation, a user has to travel back and forth between the farm and the laboratory, consuming extra time and labor; in addition, the fluorescent microscope is operated manually and the identification is conducted by a professional, therefore, the reliability of the result may be influenced by human factors.

SUMMARY OF THE INVENTION

It is an object of the present invention to provide a portable biological microscopic image analysis system suitable for analyzing a sample from an animal on a slide in real time.

Therefore, the portable biological microscopic image analysis system of the present invention comprises a handheld electronic device and a microscope kit; the handheld electronic device comprises an image capture unit, an image analysis module electrically connected to the image capture unit, and a real-time state analysis module electrically connected to the image analysis module; the microscope kit is detachably mounted on the handheld electronic device; wherein the image capture unit is used to obtain an image related to the sample through the microscope kit, the image analysis module is used to obtain cell information corresponding to the animal according to the image, and the real-time state analysis module is used to obtain state information corresponding to the animal according to the cell information.

Wherein the microscope kit comprises a base formed with a slide slot where the slide is inserted.

The portable biological microscopic image analysis system further comprises a server communicatively connected to the handheld electronic device, the server comprises a data read/write module and an individual animal history database electrically connected to the data read/write module, the handheld electronic device is also used to transmit the cell information corresponding to the animal to the server, and the data read/write module of the server is used to write the cell information corresponding to the animal into the individual animal history database.

Wherein the server further comprises an species-level history database electrically connected to the data read/write module, the species-level history database is provided with a plurality of species data groups, each of the species data groups is related to an animal species, and the data read/write module is also used to write the cell information corresponding to the animal into the species data group related to the animal species to which the animal belongs.

Wherein the server further includes a treatment database electrically connected to the data read/write module, the treatment database is provided with a plurality of species treatment data groups, and each of the species treatment data groups is related to an animal species.

Wherein the server further comprises an advanced state learning/analysis module electrically connected to the data read/write module, the advanced state learning/analysis module is used to obtain the cell information corresponding to the animal, the species data group related to the species of the animal to which the animal belongs, and the species treatment data group related to the species of the animal to which the animal belongs, respectively; and the advanced state learning/analyzing module is also used to obtain advanced analysis information corresponding to the animal on the basis of the cell information corresponding to the animal, the species data group related to the species of the animal to which the animal belongs, and the species treatment data group related to the species of the animal to which the animal belongs.

Wherein the server further comprises an analysis history database electrically connected to the data read/write module, the analysis history database is provided with a plurality of species analysis data groups, each of the species analysis data groups is related to an animal species, and the advanced state learning/analyzing module is also used to write the advanced analysis information corresponding to the animal into the species analysis data group related to the animal species to which the animal belongs.

The present invention has the following advantageous effects: a user can obtain the cell information and the state information corresponding to the animal in real time through the handheld electronic device and the microscope kit; moreover, the server utilizes the individual animal history database, the species-level history database, and the treatment database to compute, whereby the advanced analysis information corresponding to the animal can be obtained by the user who may then have a further and fuller understanding of the status quo of the animal and possible treatments to the same.

BRIEF DESCRIPTION OF THE DRAWINGS

Other features and advantageous effects of the present invention will be apparent from the embodiments with reference to the drawings, in which.

DETAILED DESCRIPTION OF THE INVENTION

The foregoing and other aspects, features and advantages of the present invention will be apparent from the following detailed description of a preferred embodiment, taken in conjunction with the accompanying drawings.

Figure 1:
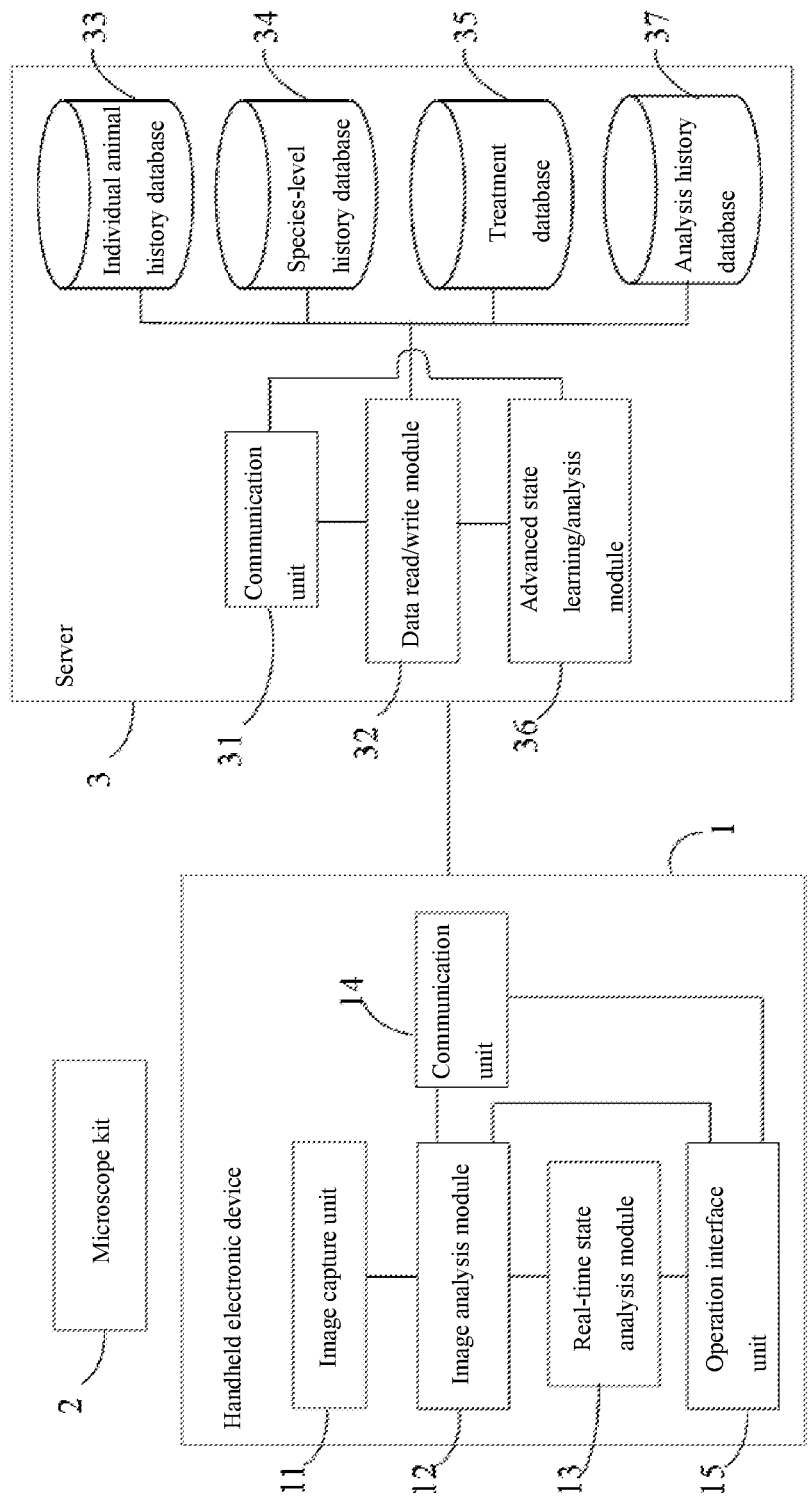
FIG. 1 is a block diagram illustrating a preferred embodiment of a portable biological microscopic image analysis system according to the present invention.
Figure 2:
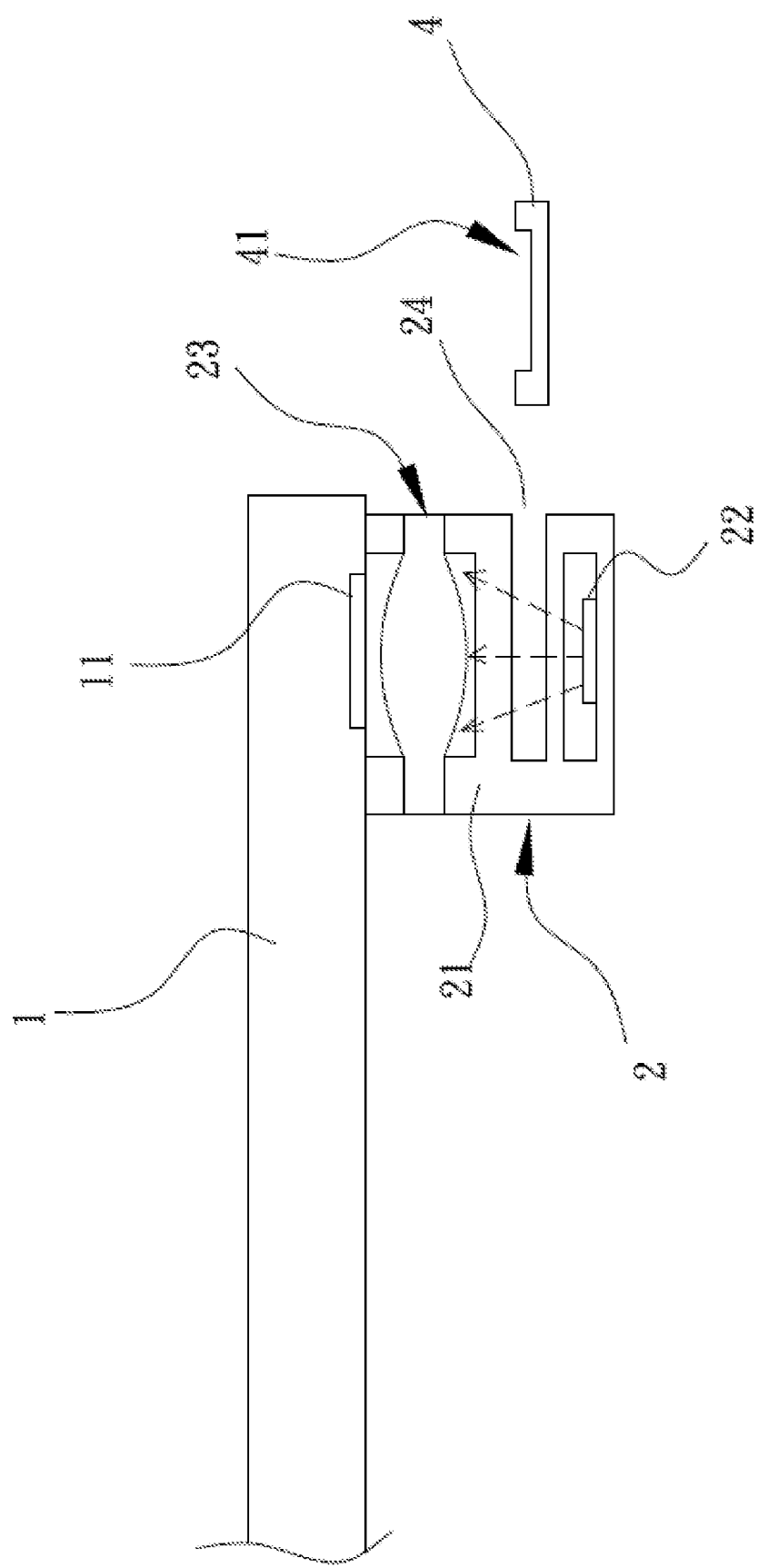
FIG. 2 is a schematic structural diagram illustrating a handheld electronic device and a microscope kit in the portable biological microscopic image analysis system.

Referring to FIGS. 1 and 2, a portable biological microscopic image analysis system according to the present invention comprises a handheld electronic device 1, a microscope kit 2 detachably mounted to the handheld electronic device 1, and a server 3 communicatively connected to the handheld electronic device 1. In the preferred embodiment, the hand-held electronic device 1 can be a smartphone, and an existing mobile phone plug-in microscope may be used as the microscope kit 2.

The handheld electronic device 1 comprises an image capture unit 11, an image analysis module 12 electrically connected to the image capture unit 11, a real-time state analysis module 13 electrically connected to the image analysis module 12, a communication unit 14 electrically connected to the image analysis module 12, and an operation interface unit 15 electrically connected to the image analysis module 12, the real-time state analysis module 13 and the communication unit 14.

The microscope kit 2 comprises a base 21, a light-emitting element 22 provided on the base 21, a lens group 23 provided on the base 21, and a slide slot 24 formed in the base 21; the light-emitting element 22 is more distant from the image capture unit 11 relative to the lens group 23, and the slot 24 is located between the light-emitting element 22 and the lens group 23.

The server 3 comprises a communication unit 31, a data read/write module 32 electrically connected to the communication unit 31, an individual animal history database 33 electrically connected to the data read/write module 32, an species-level history database 34 electrically connected to the data read/write module 32, a treatment database 35 electrically connected to the data read/write module 32, an advanced state learning/analysis module 36 electrically connected to the communication unit 31 and the data read/write module 32, and an analysis history database 37 electrically connected to the data read/write module 32. Wherein individual animal history database 33 has multiple pieces of cell information of individual animals; the species-level history database 34 has a plurality of species data groups, each of the species data groups is related to an animal species; the treatment database 35 has a plurality of species treatment data groups, each of the species treatment data groups is related to an animal species; the analysis history database 37 has a plurality of species analysis data groups, each of the species analysis data groups is related to an animal species.

A user can analyze an animal in real time with the portable biological microscopic image analysis system without being limited by actual field situations, and the following examples are provided to further illustrate the operation of the components of the system.

Figure 3:
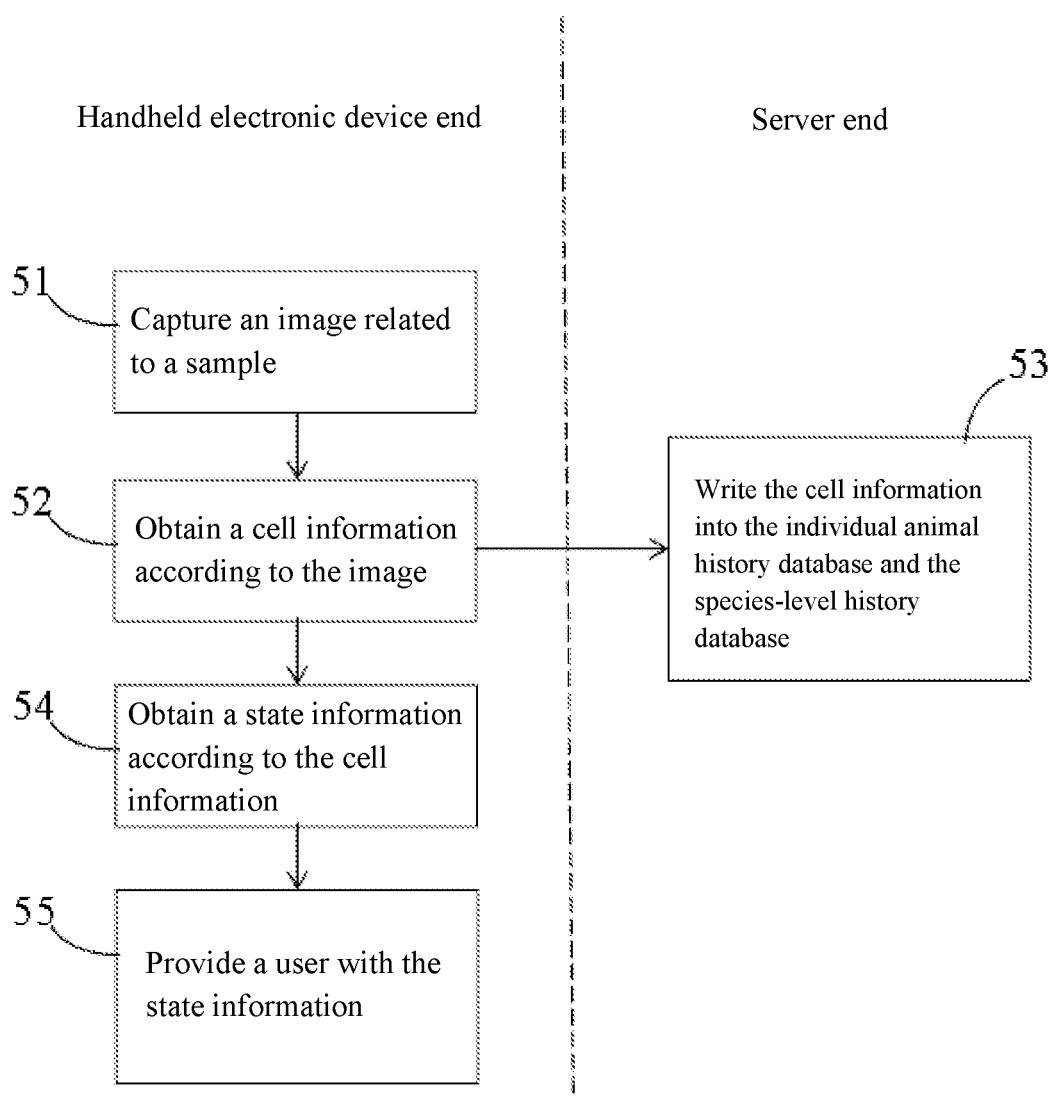
FIG. 3 is a flow chart illustrating an example of use of the portable biological microscopic image analysis system for in-situ sampling analysis.

Referring to FIGS. 1, 2 and 3, when a user needs to sample and analyze an animal in a farm, the animal can be sampled on the spot, and a sample (not shown) from the animal can be analyzed in real time with a slide 4; wherein, the slide 4 is inserted into the slot 24 of the base 21 of the microscope kit 2, and the slide 4 is formed with a recess 41 for placing the sample.

As shown in step 51, the image capture unit 11 of the handheld electronic device 1 captures an image related to the sample through the microscope kit 2; in the preferred embodiment, the image is a phase contrast image.

As shown in step 52, the image analysis module 12 of the handheld electronic device 1 obtains cell information corresponding to the animal according to the image, and the handheld electronic device 1 also transmits the cell information to the server 3 through the communication unit 14. In the preferred embodiment, the image analysis module 12 obtains a cell segmentation image from the image, and obtains an area proportion of the cell and a quantity of disconnected components of the cell from the cell segmentation image; the cell information includes the area proportion the cell and the quantity of disconnected components of the cell. It should be noted that the algorithmic model employed by the image analysis module 12 is implemented by conducting machine learning of a plurality of images for training without using fluoro-stained images for model learning so that the handheld electronic device 1 requires less information to be processed, and the lightweight computation thereof caters to the computational limitations of other types of portable or mobile electronic devices (not shown) in addition to the handheld electronic device 1.

As shown in step 53, the data read/write module 32 of the server 3 is used to write the cell information corresponding to the animal received by the communication unit 31 into the individual animal history database 33 and the species data group in the species-level history database 34 related to the species of the animal to which the animal belongs.

As shown in step 54, the real-time state analysis module 13 of the handheld electronic device 1 is used to obtain state information corresponding to the animal according to the cell information corresponding to the animal; wherein the rules of computation performed by the real-time state analysis module 13 are established in advance and may vary according to different animal species. For example, the state information corresponding to the animal may be an estrus cycle in which the animal is currently experiencing.

As shown in step 55, the operation interface unit 15 of the handheld electronic device 1 is used to provide the user with the cell information and the state information corresponding to the animal so that the user can know the real-time analysis information of the animal.

Figure 4:
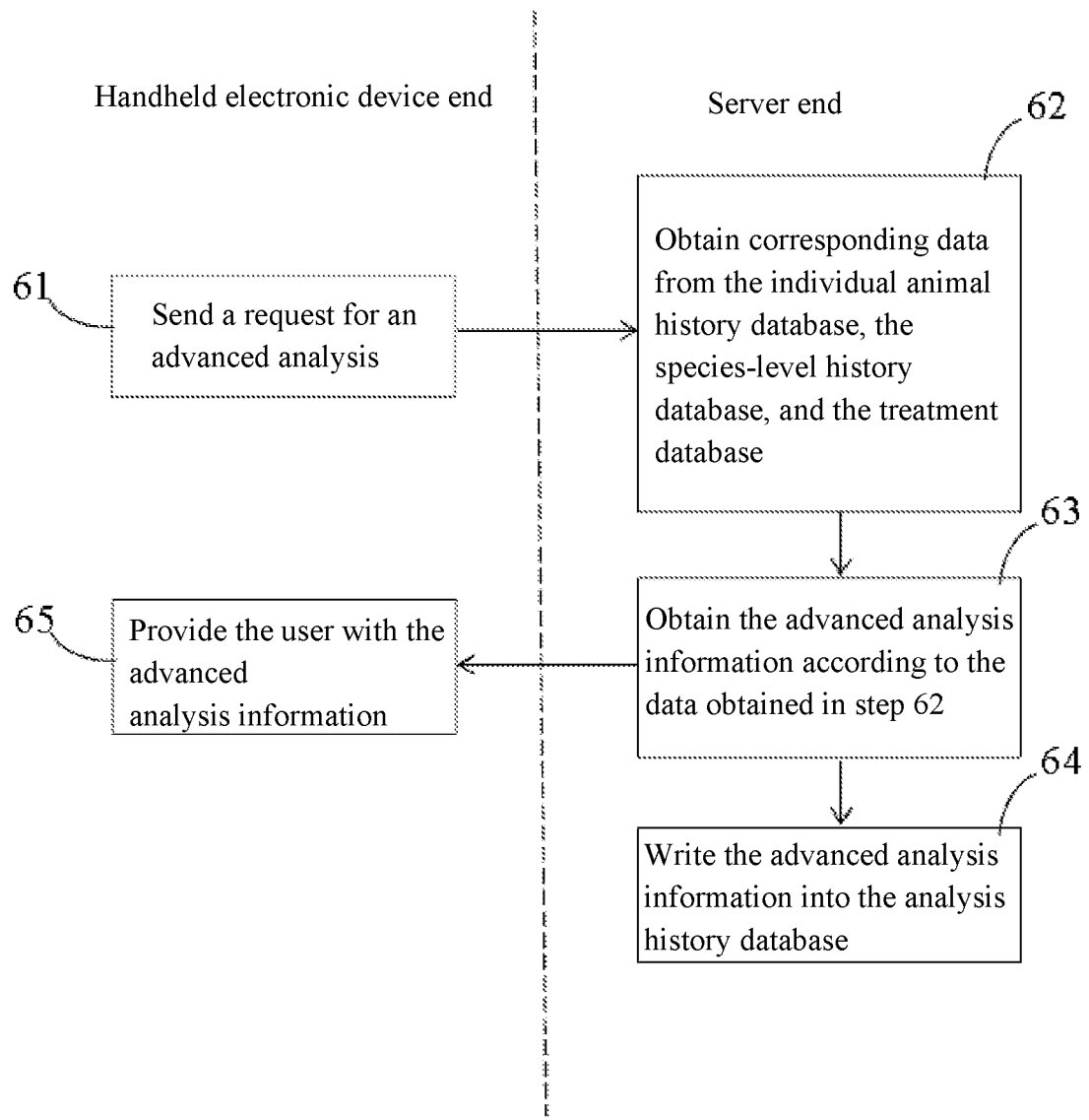
FIG. 4 is a flow chart illustrating an example where a user obtains advanced analysis information using a server of the portable biological microscopic image analysis system.

Referring to FIGS. 1 and 4, when the user desires further information about the animal, he may operate the operation interface unit 15 of the hand-held electronic device 1 to issue a request for an advanced analysis through the communication unit 14, as shown at step 61.

As shown in step 62, the communication unit 31 of the server 3 receives the request for the advanced analysis, and the data read/write module 32 obtains the cell information corresponding to the animal, the species data group related to the species of the animal to which the animal belongs, and the species treatment data group related to the species of the animal to which the animal belongs from the individual animal history database 33, the species-level history database 34 and the treatment database 35, respectively, according to the request for the advanced analysis.

As shown in step 63, the advanced state learning/analysis module 36 of the server 3 is also used to obtain advanced analysis information corresponding to the animal according to the data obtained in step 62, and transmitting the advanced analysis information corresponding to the animal to the handheld electronic device 1 through the communication unit 31. It should be noted that because the advanced state learning/analysis module 36 does not obtain the result of the analysis solely from the cell information of the animal, but rather from a series of history data related to the animal and the species to which the animal belongs, therefore, the result can more accurately reflect the state and behavioral characteristics of the animal. In the preferred embodiment, the advanced analysis information includes current state information, future cell information, and future state information corresponding to the animal; wherein the future cell information includes a predicted area proportion of the cell and a predicted quantity of disconnected components of the cell; the future state information refers to a prediction of the state of the animal after, for example, 12 hours or 24 hours, in the future.

As shown in step 64, the data read/write module 32 of the server 3 is also used to write the advanced analysis information corresponding to the animal into the species analysis data group in the analysis history database 37 related to the animal species to which the animal belongs. Wherein the data in the analysis history database 37 is used for comparison and correction when the advanced state learning/analysis module 36 conducts deep learning.

As shown in step 65, the operation interface unit 15 of the hand-held electronic device 1 is further used to provide the user with the advanced analysis information corresponding to the animal received by the communication unit 14 so that the user can have a further and fuller understanding of the status quo of the animal and possible treatments to the animal.

In summary, the user can obtain the cell information and the state information corresponding to the animal in real time through the handheld electronic device 1 and the microscope kit 2; moreover, the server 3 utilizes the individual animal history database 33, the species-level history database 34, and the treatment database 35 to compute, whereby the advanced analysis information corresponding to the animal can be obtained by the user who may then have a further and fuller understanding of the status quo of the animal and possible treatments to the same; therefore, the object of the present invention can really be achieved.

It is intended that the foregoing description be considered as exemplary only and not limiting as to the scope of the present invention, and any simple equivalent changes and modifications made in accordance with the scope of the application for invention and the disclosure of the description are to be embraced by the appended claims and their equivalents.

LIST OF REFERENCE NUMERALS

1 Handheld electronic device
11 Image capture unit
12 Image analysis module
13 Real-time state analysis module
14 Communication unit
15 Operation interface unit
2 Microscope kit
21 Base
22 Light-emitting element
23 Lens group
24 Slide slot
3 Server
31 Communication unit
32 Data read/write module
33 Individual animal history database
34 Species-level history database
35 Treatment database
36 Advanced state learning/analysis module
37 Analysis history database
4 Slide
41 Recess
51-55 Steps
61-65 Steps

The invention claimed is:

1. A portable biological microscopic image analysis system suitable for analyzing a sample on a slide in real time, the sample coming from an animal, the portable biological microscopic image analysis system comprising:

a handheld electronic device comprising an image capture unit, an image analysis module electrically connected to the image capture unit, and a real-time state analysis module electrically connected to the image analysis module; and a microscope kit detachably mounted on the handheld electronic device,
wherein the microscope kit comprises a base formed with a slide slot where the slide is inserted;

wherein the image capture unit is used to obtain an image related to the sample through the microscope kit, the image analysis module is used to obtain cell information corresponding to the animal according to the image, and the real-time state analysis module is used to obtain state information corresponding to the animal according to the cell information.

2. The portable biological microscopic image analysis system according to claim 1, wherein the image analysis module obtains a cell segmentation image from the image, and obtains an area proportion of a cell and a quantity of disconnected components of the cell from the cell segmentation image, the cell information comprising the area proportion the cell and the quantity of the disconnected components of the cell.

3. The portable biological microscopic image analysis system according to claim 2, further comprising a server communicatively connected to the handheld electronic device, the server comprises a data read/write module and an individual animal history database electrically connected to the data read/write module, the handheld electronic device is also used to transmit the cell information corresponding to the animal to the server, and the data read/write module of the server is used to write the cell information corresponding to the animal into the individual animal history database.

4. The portable biological microscopic image analysis system according to claim 3, wherein the server further comprises an species-level history database electrically connected to the data read/write module, the species-level history database is provided with a plurality of species data groups, each of the species data groups is related to an animal species, and the data read/write module is also used to write the cell information corresponding to the animal into the species data group related to the animal species to which the animal belongs.

5. The portable biological microscopic image analysis system according to claim 4, wherein the server further comprises a treatment database electrically connected to the data read/write module, the treatment database is provided with a plurality of species treatment data groups, and each of the species treatment data groups is related to an animal species.

6. The portable biological microscopic image analysis system according to claim 5, wherein the server further comprises an advanced state learning/analysis module electrically connected to the data read/write module, the advanced state learning/analysis module is used to obtain the cell information corresponding to the animal, the species data group related to the species of the animal to which the animal belongs, and the species treatment data group related to the species of the animal to which the animal belongs, respectively; and the advanced state learning/analyzing module is also used to obtain advanced analysis information corresponding to the animal on the basis of the cell information corresponding to the animal, the species data group related to the species of the animal to which the animal belong, and the species treatment data group related to the species of the animal to which the animal belongs.

7. The portable biological microscopic image analysis system according to claim 6, wherein the advanced analysis information comprises current state information, future cell information, and future state information corresponding to the animal.

8. The portable biological microscopic image analysis system according to claim 7, wherein the future cell information comprises a predicted area proportion of the cell and a predicted quantity of disconnected components of the cell, and the future state information refers to a prediction of the state of the animal after a period of time in the future.

9. The portable biological microscopic image analysis system according to claim 6, wherein the server further comprises an analysis history database electrically connected to the data read/write module, the analysis history database is provided with a plurality of species analysis data groups, each of the species analysis data groups is related to an animal species, and the advanced state learning/analyzing module is also used to write the advanced analysis information corresponding to the animal into the species analysis data group related to the animal species to which the animal belongs.

10. The portable biological microscopic image analysis system according to claim 9, wherein the species analysis data groups in the analysis history database are used for comparison and correction when the advanced state learning/analysis module conducts deep learning.

* * * * *